US009789305B2

(12) United States Patent
Frericks et al.

(10) Patent No.: US 9,789,305 B2
(45) Date of Patent: Oct. 17, 2017

(54) METHOD FOR PRODUCING AN ELECTRODE STRUCTURE

(71) Applicant: Heraeus Precious Metals GmbH & Co. KG, Hanau (DE)

(72) Inventors: Matthias Frericks, Hanau (DE); Lydia Buckow, Pfungstadt (DE)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 57 days.

(21) Appl. No.: 14/413,209

(22) PCT Filed: Jul. 5, 2013

(86) PCT No.: PCT/EP2013/064285
§ 371 (c)(1),
(2) Date: Jan. 6, 2015

(87) PCT Pub. No.: WO2014/006190
PCT Pub. Date: Jan. 9, 2014

(65) Prior Publication Data
US 2015/0165191 A1  Jun. 18, 2015

(30) Foreign Application Priority Data

Jul. 6, 2012 (DE) .......................... 10 2012 013 338

(51) Int. Cl.
*A61N 1/05* (2006.01)
*H01M 4/00* (2006.01)

(52) U.S. Cl.
CPC ......... *A61N 1/0541* (2013.01); *A61N 1/0534* (2013.01); *A61N 1/0551* (2013.01); *H01M 4/00* (2013.01)

(58) Field of Classification Search
CPC .................................................... A61N 1/0534
See application file for complete search history.

(56) References Cited

U.S. PATENT DOCUMENTS

| 4,762,135 A | 8/1988 | van der Puije et al. |
| 6,074,422 A | 6/2000 | Berrang et al. |
| 8,010,208 B2 | 8/2011 | Nimer et al. |

(Continued)

FOREIGN PATENT DOCUMENTS

EP  1488827  12/2004

OTHER PUBLICATIONS

Search Report and Written Opinion for International Application No. PCT/EP2013/064285 mailed Apr. 11, 2013 (9 pgs).

*Primary Examiner* — Carl H Layno
*Assistant Examiner* — Jennifer Ghand
(74) *Attorney, Agent, or Firm* — Dicke, Billig & Czaja, PLLC

(57) ABSTRACT

The invention relates to a process for production of an electrode structure, including: producing a longitudinal body having a core and at least one layer made of an electrode material surrounding the core; removing a part of the layer made of electrode material while forming a plurality of electrodes that are arranged such as to be distributed in the longitudinal direction and which are separated from each other, and contact paths that extend in the longitudinal direction and adjoin the electrodes, each, as the same part; applying a layer made of a polymeric material while embedding, at least in part, the electrodes and/or contact paths.

13 Claims, 6 Drawing Sheets

(56) References Cited

U.S. PATENT DOCUMENTS

| | | | |
|---|---|---|---|
| 2007/0282410 A1* | 12/2007 | Cross | A61N 1/05 607/116 |
| 2010/0072659 A1* | 3/2010 | Gellman | A61F 2/88 264/209.1 |
| 2010/0094387 A1* | 4/2010 | Pianca | A61N 1/0553 607/116 |
| 2010/0114278 A1* | 5/2010 | McMorrow | A61N 1/0553 607/116 |
| 2010/0305673 A1 | 12/2010 | Jolly et al. | |
| 2011/0072659 A1* | 3/2011 | Swanson | A61N 1/05 29/885 |

* cited by examiner

METHOD FOR PRODUCING AN ELECTRODE STRUCTURE

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

The invention relates to a process for producing an electrode structure according to the features of claim 1 and to an electrode structure according to the generic part of claim 15.

EP 1 488 827 A1 describes a process for producing an electrode structure, in particular a cochlear electrode to be introduced into an inner ear, in which a planar layer made of an electrode material is applied onto a planar support material and is structured into individual electrodes which are arranged such as to be distributed in a longitudinal direction and have contact paths adjoining them in the same part.

It is the object of the invention to specify a process for producing an electrode structure that enables the production of electrode structures of high quality.

Said object is met according to the invention through a process for producing an electrode structure, comprising the steps of:
  a. Producing a longitudinal body having a core and at least one layer made of an electrode material surrounding the core;
  b. Removing a part of the layer made of electrode material while forming a plurality of electrodes that are arranged such as to be distributed in the longitudinal direction and which are separated from each other, and contact paths that extend in the longitudinal direction and adjoin the electrodes, each, as the same part;
  c. Applying a layer made of a polymeric material while embedding, at least in part, the electrodes and/or contact paths formed in step b.

In the scope of the invention, the electrodes and contacts paths are formed as one-part structures that differ from each other in their shape and/or function, at least after step b. In this context, the contact paths mainly serve for electrically conductive connection of the electrodes over a spatial distance in the longitudinal direction, for example to other conductors, a supply circuitry or the like. The electrodes have a different function than the contact paths. They serve, for example, for electrical connection to biological tissue, for example nerve cells, or as a component of a sensor, in particular a sensor having a multi-layered structure.

The contact paths extending in the longitudinal direction shall be understood to mean any bridging of a distance in said direction. Pertinent examples include a straight extension parallel to the longitudinal direction or a helical extension about the longitudinal direction.

It it feasible, by means of the process according to the invention, as a matter of principle, to structure the electrodes directly in their spatial position with respect to a circumferential direction about the core. As a result, the layer surrounding the electrodes can be provided to be seamless in the circumferential direction, if needed.

Often and/or in a particularly simple design, the electrode material has a hollow cylindrical cross-section, for example while covering a circular core. Generally, according to the scope of the invention, the layer can take any hollow shape about a core of corresponding external circumference according to requirements, for example an elliptical or polygonal cross-section.

It is generally preferred to apply the layer made of electrode material mechanically to the core as a solid material, which attains good strength and flexibility and flexibility upon stress reversal of the resulting electrodes and contact paths. In principle, though, other ways of applying the layer are feasible as well, for example vapour deposition, electroplating, etc.

It is generally preferred, but not mandatory, to use electrode structures according to the invention on the human body. A typical application is the use as a cochlear electrode in inner ear implants. Another application is as a stimulation electrode in the central nervous system, such as in the methods of "deep brain stimulation" in the brain or "spinal cord stimulation" in the spinal cord (pain therapy).

Furthermore, electrode structures according to the invention can serve as the basis of sensor applications, such as by building-up the electrodes into sensors by further layers and/or overlapping design.

It is generally advantageous for electrode structures according to the invention to have lengths in the range of 1 cm to more than 10 cm at a relative small diameter in the order of 1 mm. The high aspect ratio of length and diameter as well as the small size of the structures contribute to the particular suitability of the process according to the invention. Preferred thickness values of the layer made of electrode material depend on the requirements and are, for example, in the range of 0.05 mm to 0.3 mm. This can be provided, for example, for typical applications for electrical connection to nerve cells. But considerably smaller thickness values are also conceivable, for example down to less than 0.001 mm. Structures this thin can, in particular, be a component of a sensor.

The electrode material preferably consists of a bio-compatible metal, in particular for use on the human body. Pertinent examples include platinum and alloys thereof, in particular PtIr alloys, PtW alloys, gold and gold alloys, tantalum, titanium, niobium or other suitable materials. Depending on requirements, the layer made of electrode material can just as well be composed of multiple layers made of different materials.

In a preferred embodiment of the invention, the core is removed after step c and the resulting hollow space is filled, at least partly, with a material, which preferably is polymeric, while forming a new core. This renders the manufacture simple, since the core material can be adapted to the production requirements regarding the mechanical and/or chemical properties. Preferably, the core to be removed later consists of a metal, in particular copper. With respect to the provision of the longitudinal body, methods are known and established, for example from the field of cardiovascular electrodes, that involve the application of bio-compatible metals, such as PtIr, by means of a drawing die onto a round copper core to form a two-layer wire with a bio-compatible outer layer. A wire of this type can serve, for example, as starting material for the purposes of step a. After embedding of the electrodes and contact paths in a polymeric material, the core can be removed, for example by etching. The resulting hollow structure is expediently being filled with a new core, to provide a desired mechanical property and/or to insulate the electrodes from the inner side as well. The new core can be implemented, for example, by casting thermally or otherwise curing polymer or by inserting a sub-calibre tube and subsequent expansion.

In an alternative embodiment, the core is not removed after step c. Cores of this type are preferably, but not necessarily, made of an electrically insulating polymeric material, for example the same material as the outer polymer layer. But it is also conceivable that the core has an inhomogeneous structure. A core of this type can consist, for example, of a metal or glass fibres, etc. on the inside and be enveloped by an insulating layer onto which the layer made of electrode material is applied.

In a preferred embodiment of the invention, step b. is implemented by erosive removal of the electrode material. It is particularly advantageous for the erosive removal to proceed by means of a laser, especially an ultra-short pulse laser, or by means of spark erosion. According to the scope of the invention, an ultra-short pulse laser, the use of which is preferable, shall be understood to be a laser whose energy density is increased by temporal compression of its pulse duration. According to a particularly preferred embodiment, the ultra-short pulse laser is a femtosecond laser. This allows scanning, computer-controlled processes to be used that are effective and can be implemented in few or only one step. Modern femtosecond lasers are particularly well-suited for metal-working, since the high energy density results in direct sublimation of the metal removed such that the selectivity is high. In particular, the core situated under the electrode material is affected only minimally such that undesirable effects, such as degeneration of a polymeric core or contamination of the electrode material by a metallic core is minimised.

An alternative to this embodiment provides step b to be implemented by means of a photochemical process. Presently, a photochemical process shall be understood to be any process, in which a structured change in a material property is generated by means of an illumination such that a material can be structured by subsequent chemical process steps. Pertinent examples include photolithography processes of semiconductor manufacturing. The photochemical process preferably comprises the illumination of a layer situated on the electrode material by a laser. For example, the laser can illuminate, in a scanning and computer-controlled manner, a photoresist that is applied to the electrode material. As an alternative photochemical process in place of a gridded light beam, an imaging illumination is conceivable as well. As an alternative to the use of a photoresist and illumination and/or as an alternative to the application of a photo-chemical process, it is also conceivable that a masking layer for subsequent etching processes is applied directly onto the electrode material by means of scanning-printing processes. For further processing of electrode material with a textured and/or illuminated mask, please refer to printed specification EP 1 488 827 A1 also.

It is generally advantageous to provide that step c proceeds by extrusion of the polymeric material, by printing the material, by application to the entire surface from liquid phase or by deposition from the gas phase. The polymeric material may be any polymeric material according to requirements, preferably it can be bio-compatible. Examples of suitable materials include silicone, polyimide (PI), polyurethane (PU) or parylene, in particular parylene C. The latter are deposited directly from the gas phase in an appropriate device and have well-known applications in the field of bio-compatible implants. Polyimide can be applied, for example, in a particularly simple embodiment in the manner of a dip coating process. Silicone and other suitable materials can be applied, for example, by extrusion or by printing. In particular, structured scanning printing processes can be preferred presently, since they allow coverage of the electrode surfaces by the polymeric material to be avoided.

It is generally advantageous for one embodiment of the invention to comprise the step of selective removal of the layer applied in step c., at least in regions of the electrodes. Preferable, but not necessarily, this can take place by means of a laser. In particular, this can be the same laser, by means of which the layer was removed in step b, optionally after adjustment of operating parameters of the laser. Thereby, a galvanic contact of the electrode to the surroundings is enabled. In this sense, said step is required only if the embedding of the formed structures in the polymer layer took place over the entire surface and non-selectively, but may also be desired even then for the purpose of quality optimisation.

It is generally advantageous for the invention to comprise the step of bending the longitudinal body about the longitudinal direction into a shape, in particular after step b or after step c. In the case of cochlear electrodes, the shape can be a defined pre-bending into a coil.

In a possible refinement, the invention provides the layer made of electrode material to be surrounded by a second layer made of an electrode material, whereby the layers made of electrode material are separated by an insulating layer. This enables a multi-layered structure that renders, for example, a particularly large number of electrodes and contact paths feasible. Thus, a portion of the electrodes and contact paths can be embedded in a first radially inner layer of insulating layers and another portion can be embedded in a radially outer layer.

A possible refinement of the invention provides the longitudinal body to taper at least over a section in the longitudinal direction. A taper of this type can be provided for example, in cochlear electrodes in order to design the electrode structure in the inner ear region to be particularly flexible and susceptible to minimally invasive processes. For example, the electrode can be tapered in an end section over a distance of approximately 1 cm from 1.5 mm in diameter to 0.5 mm in diameter.

Obviously, an electrode structure according to the invention can comprise further features and process steps, such as, for example, purification steps, the attachment of a tip at one end of the electrode structure or the connection of the contact paths to an adjoining structure, e.g. to a feed line or directly to a control unit. In the case of cochlear electrodes, it is particularly advantageous for cost reasons, that the electrode structure plus the contact paths have a sufficient length, for example on the order of 10 cm, to allow for direct connection to a control unit.

The object of the invention is also met through an electrode structure, comprising
   a longitudinal body having a non-conductive layer that has a hollow shape, and
   a plurality of electrodes that are embedded in the layer such as to be insulated from each other, and a plurality contact paths that extend in the longitudinal direction and are insulated with respect to the outside by the layer, and are each connected, being a single part, to one of the electrodes, whereby the non-conductive layer is formed to be seamless in circumferential direction.

An electrode structure of this type is preferably, but not necessarily, produced by a process according to the invention.

In the scope of the invention, a hollow shape shall be understood to mean any shape of cross-section that can be selected freely depending on the application on hand. For many applications, the insulating layers will have a hollow cylindrical shape such that the cross-section of the layer consists of concentric circles. In other examples, the shape of the cross-section can just as well be polygonal or elliptical.

Providing the layer embedding the electrodes in an insulating manner to be seamless in circumferential direction improves the stability and/or security against damage and compatibility due to the absence of interfering seams. The absence of seams in circumferential direction shall be understood to mean that the electrode structure comprises no seam that extend in longitudinal direction and are a disturbance as viewed in circumferential direction, at least over a substantial part of its functionally relevant sections.

A preferred refinement of the electrode structure provides the electrodes to each comprise a surface beyond which the surface of the layer made of polymeric material protrudes. Preferably, but not necessarily, an edge section of the electrodes is framed by the layer. Since the insulating layer usually consists of a softer material than the electrodes, this improves the compatibility. In addition, the framing of the edges reduces the risk of inadvertent projection of the electrodes from the insulating layer, which may involve hazards when used in the human body.

Further advantages and features of the invention are evident from the exemplary embodiment described in the following as well as the dependent claims.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

Further features and of the can be derived from the following execution example as well as from the attached claims.

Figure 1:
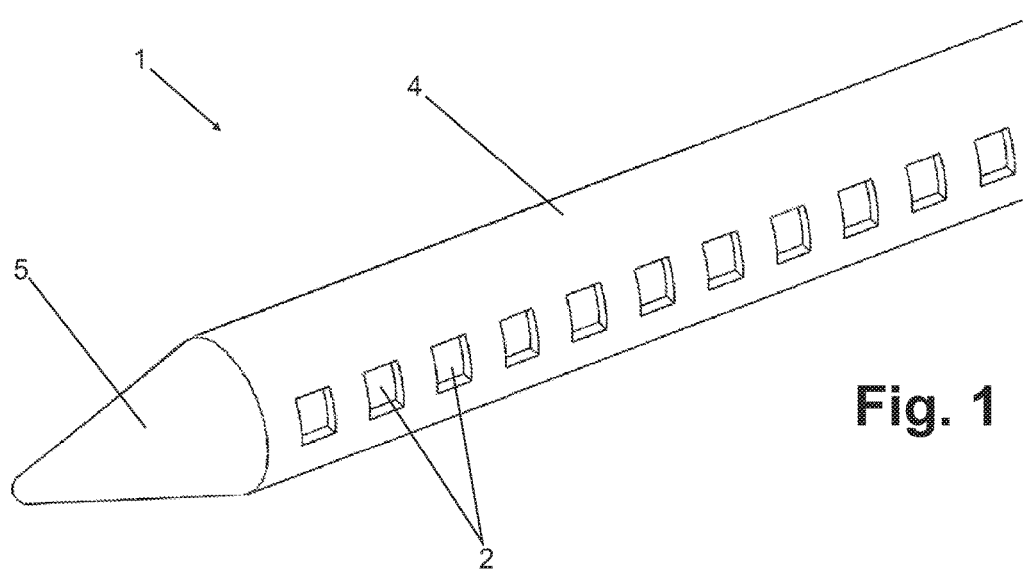

One preferred exemplary embodiment of the invention is described in the following and illustrated in more detail based on the appended drawings. In the figures:

FIG. 1 shows a schematic spatial view of an electrode structure according to the invention, presently for use as a cochlear electrode.

Figure 1A:
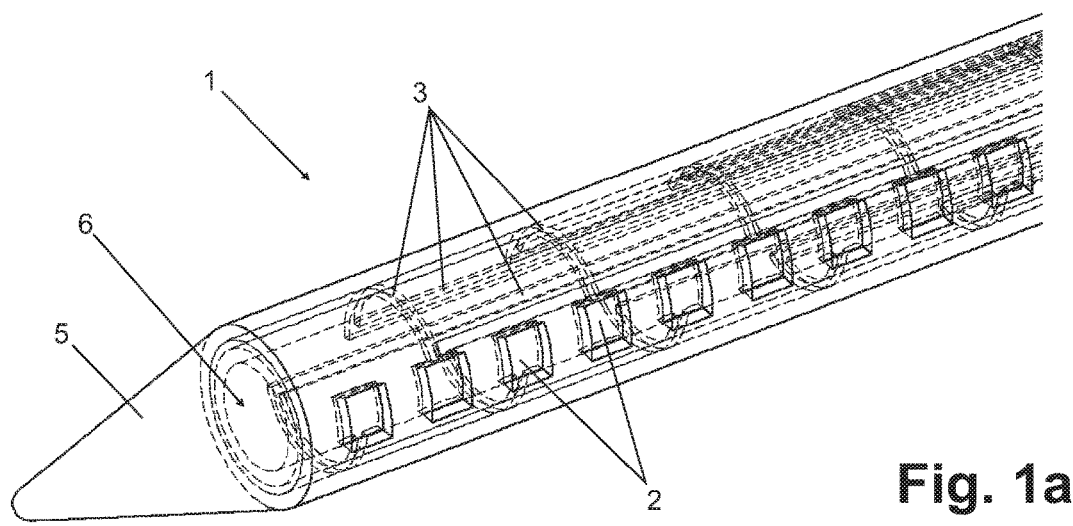

FIG. 1a shows the electrode structure of FIG. 1 with lines hidden.

Figure 2:
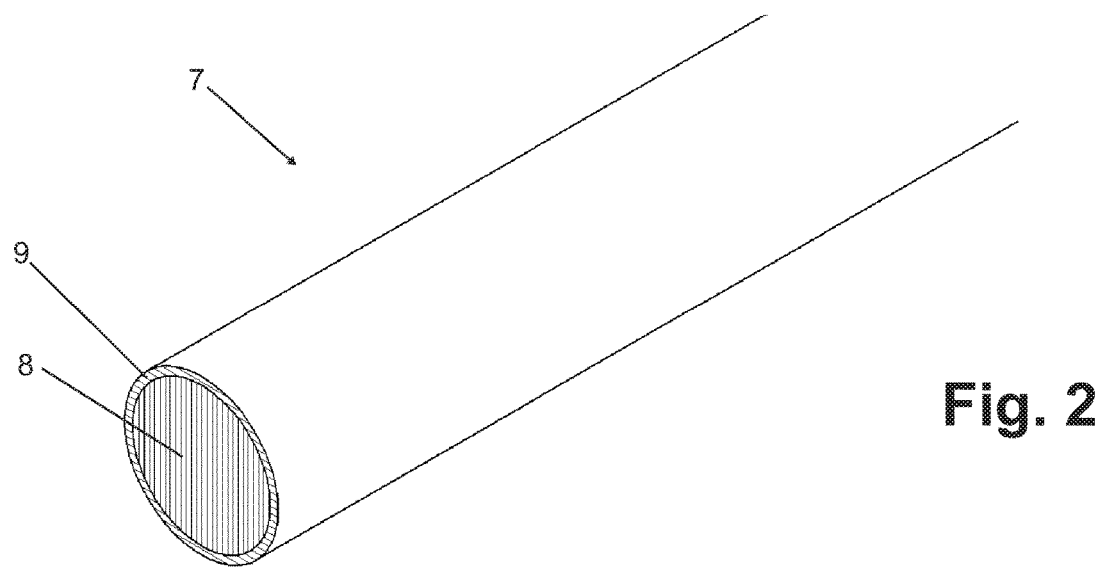

FIG. 2 shows a precursor of the electrode structure of FIG. 1a.

Figure 3:
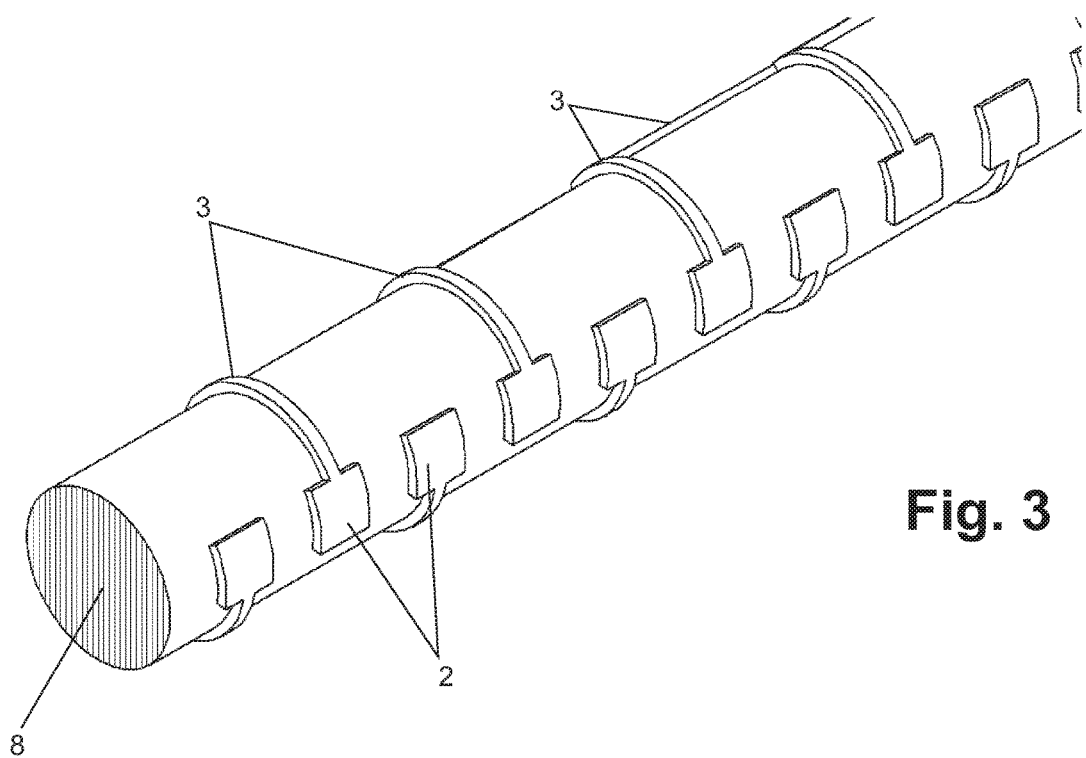

FIG. 3 shows the precursor of FIG. 2 after one further process step.

Figure 4:
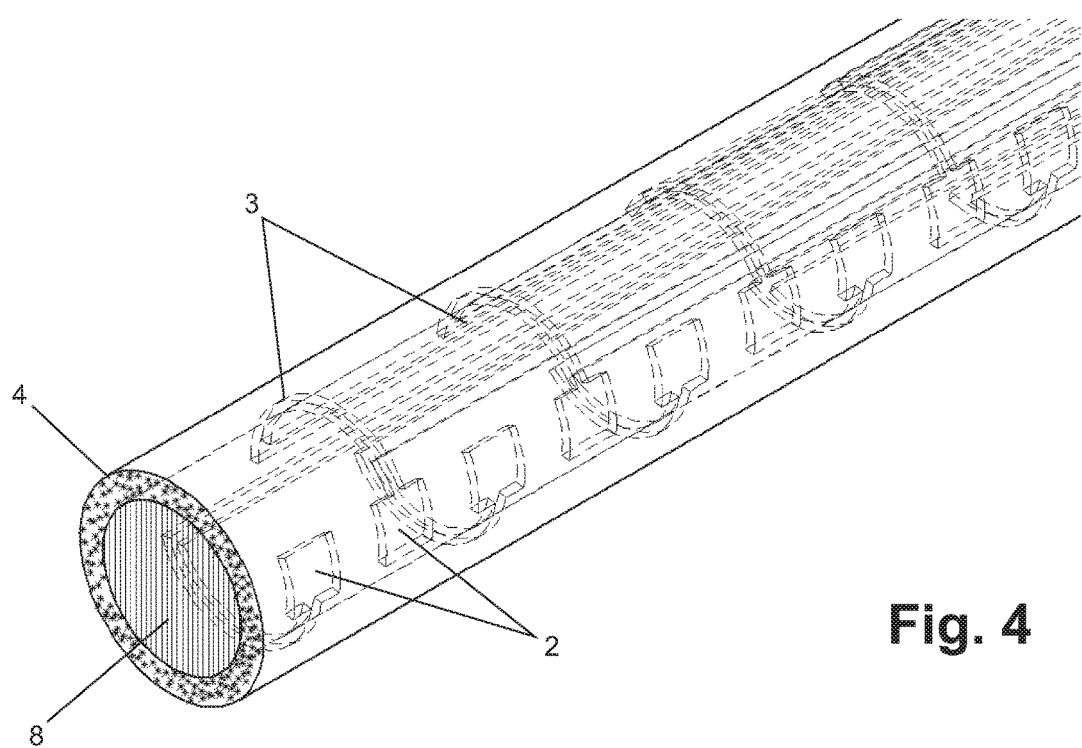

FIG. 4 shows the precursor of FIG. 3 after one further process step.

Figure 5:
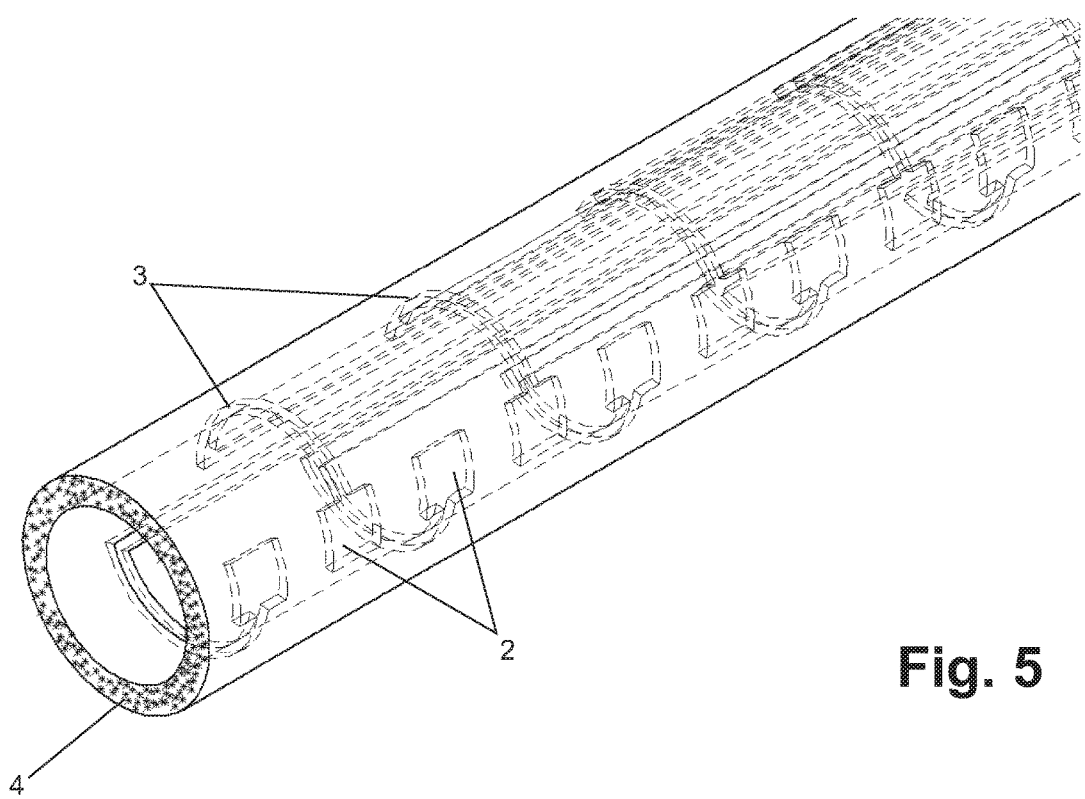

FIG. 5 shows the precursor of FIG. 4 after one further process step.

An electrode structure according to the invention according to FIG. 1 is used as a cochlear electrode for implantation in the human inner ear. FIG. 1 shows a front section 1 of the electrode that is introduced into the inner ear. With regard to diameter and material, the electrode is designed to have a defined stiffness in order to conform to the helical shape in the inner ear. For this purpose, the electrode structure can just as well be pre-bent and/or taper toward its front end.

The electrode structure 1 extends in a longitudinal direction, whereby a plurality of electrodes 2 is arranged in the longitudinal direction at a distance from each other. Presently, the electrodes 2 are provided as flat metallic plates with a rectangular circumference, but can also be of a different shape.

One contact path 3 is connected to each of the electrodes 2 such that it is the same part made of uniform material. The contact paths extend from the first electrode by a defined distance in the circumferential direction and then substantially parallel to each other and in the longitudinal direction. Presently, the electrodes 2 and contact paths 3 consist of a bio-compatible PtIr alloy. In alternative embodiments, it is conceivable that the contact paths have a different extension, for example, a helical extension. In any case, the contact paths effect electrical connection of the respective electrode over a distance in the longitudinal direction in this context.

The electrodes 2 and the contact paths 3 are embedded in an outer insulating layer 4 of the electrode structure. In this context, the surfaces of the electrodes 2 are exposed towards the outside, whereas the contact paths are coated with a sufficient thickness of layer 4 for insulation.

The electrode has, at its front end, a suitably shaped tip 5, which presently is attached in a separate process step.

It is obvious that the electrode can extend further through at its end facing away from the tip for basically any length. The invention can just as well provide that only the contact paths extend further over a defined section to enable connection to an extension piece or direct connection to a control unit.

The insulating layer 4 with the electrodes 2 and the contact paths 3 also envelopes a core 6 that has a circular cross-section. The core 6 consists of an insulating material. In the present case, both the layer 4 and the core 6 consist of bio-compatible silicone. The layer 4 envelops the core in circumferential direction in seamless manner, as is also apparent from the preferred production process described below.

A first process step a for the production of the electrode structure described above comprises the provision of a longitudinal body 7 made of a core 8 and a closed layer 9 that surrounds the core 8 and is made of the electrode material PtIr (see FIG. 2).

Presently, the core consists of copper and is cylindrical. The electrode material can be applied as a hollow cylindrical layer 9 that rests on or adheres firmly to the copper core 8 in a known manner by means of a drawing die. The diameter of the longitudinal body according to FIG. 2 is typically approximately 1 mm at a thickness of the layer 9 of approximately 0.1 mm and corresponds to a known wire, such as is used for special applications in the field of cardiology.

The longitudinal body is clamped in a holder (not shown) and subsequently the tightly adherent layer 9 is structured by means of an ultra-short pulse laser for metal working. Presently, this is a femtosecond laser. Ideally, the ultra-short pulse laser causes mainly direct sublimation of the bombarded material without evaporation from a liquid phase that is generated first. This is achieved by the high energy density in the laser pulse and has a positive effect in that less thermal energy is introduced into deeper layers. In this context, the layer 9 is removed by scanning bombardment by the laser down to the copper core 8, whereby the electrodes 2 and the contact paths 3 remain and/or are formed. A longitudinal body 7 after this processing step b is shown in FIG. 3.

Subsequently, the polymeric layer 4 made of silicone is applied onto longitudinal body 7 that is structured in accordance with FIG. 3. This can be done, for example, by extrusion or by printing-on the layer 4 by means of a texturing or full-surface printing process. A longitudinal body 7 after this processing step c is shown in FIG. 4.

Subsequently, the copper core 8 is removed from the longitudinal body, for example by a chemical etching process. What remains (see FIG. 5) is the substantially hollow cylindrical layer 4 with the electrodes 2 and contact paths 3 embedded therein which are positioned according to the final electrode structure.

Subsequently, the new core 6 made of insulating material, in this case silicone as before, is introduced into said hollow cylindrical layer 4.

Subsequently, the tip 5 can be attached such that, overall, the electrode structure according to FIG. 1 was produced.

If the silicone was applied to the entire surface in step c, such that the electrodes 2 are coated with a thin polymer layer, the electrodes are exposed at a suitable place again after step c. This can be done, for example, right after step c, for example by scanning removal of the polymer with a laser. In principle, this can involve the same laser and the same apparatus as for production of the electrodes 2 in step b. Alternatively, this can also involve a mechanical removal. Still alternatively, it is feasible to degenerate the polymer, i.e. presently silicone, with a suitable wavelength, e.g. in the UV range, in structured manner and to subsequently removed it from the electrodes by chemical means.

Depending on the choice of parameters for application of layer 4, the surfaces of the electrodes are arranged below the surface of layer 4 with the distance being the thickness of the cover that has been removed. If necessary, a deliberate overlap of layer 4 over the edges of the electrodes 2 can be effected.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

The invention claimed is:

1. A method for producing an electrode structure comprising:
    a. producing a longitudinal body having a core and at least one layer made of an electrode material surrounding the core;
    b. removing a part of the layer made of electrode material while forming a plurality of electrodes that are arranged such as to be distributed in a longitudinal direction and which are separated from each other, and contact paths that extend in the longitudinal direction and adjoin the electrodes, each, as the same part; and
    c. applying a layer made of a polymeric material while embedding, at least in part, the electrodes and/or contact paths formed in step b;
    characterized in that the core is removed after step c and in that a resulting hollow space is filled, at least partly, with a material while forming a new core.

2. The method according to claim 1, characterized in that the con consists of a metal.

3. The method according to claim 1, characterized in that step b is implemented by erosive removal of the electrode material.

4. The method according to claim 3, characterized in that the erosive removal proceeds by means of a laser or spark erosion.

5. The method according to claim 4, characterized in that the removal proceeds by means of an ultra-short pulse laser.

6. The method according to claim 1, characterized in that step b is implemented by means of a photochemical process.

7. The method according to claim 1, characterized in that step c proceeds by extrusion of the polymeric material, by printing the polymeric material, by application from a liquid phase or by deposition from a gas phase.

8. The method according to claim 1, characterized by selective removal of the polymeric layer applied in step c., at least in regions of the electrodes.

9. The method according to claim 1, comprising bending the longitudinal body about the longitudinal direction into a shape.

10. The method according to claim 1, characterized in that the at least one layer made of electrode material is surrounded by a second layer made of an electrode material, whereby the at least one layer and the second layers made of electrode material are separated by an insulating layer.

11. The method according to claim 1, characterized in that the longitudinal body tapers at least over a section in the longitudinal direction.

12. The method according to claim 1, characterized in that the electrode structure produced by the method is provided as cochlear electrode for arrangement in an inner ear.

13. The method according to claim 1, characterized in that at least some of the electrodes are provided as part of a sensor.

* * * * *